United States Patent [19]

Rahul

[11] Patent Number: 5,411,524
[45] Date of Patent: May 2, 1995

[54] METHOD AND APPARATUS FOR SYNCHRONIZATION OF ATRIAL DEFIBRILLATION PULSES

[75] Inventor: Mehra Rahul, Stillwater, Minn.

[73] Assignee: Medtronic, Inc., Minneapolis, Minn.

[21] Appl. No.: 148,077

[22] Filed: Nov. 2, 1993

[51] Int. Cl.⁶ ............................................. A61N 1/39
[52] U.S. Cl. ............................................. 607/4; 607/5
[58] Field of Search ....................................... 607/4, 5

[56] References Cited

U.S. PATENT DOCUMENTS

| | | | |
|---|---|---|---|
| 5,193,536 | 3/1993 | Mehra | 607/4 |
| 5,269,298 | 12/1993 | Adams et al. | 607/5 |
| 5,282,836 | 2/1994 | Kreyenhagen | |

Primary Examiner—William E. Kamm
Assistant Examiner—Kennedy J. Schaetzle
Attorney, Agent, or Firm—Reed A. Duthler; Harold R. Patton

[57] ABSTRACT

A method and apparatus for detecting and treating atrial fibrillation. In response to detecting atrial fibrillation, the device derives an escape interval based on one or more preceding intervals between ventricular depolarizations. The escape interval is initiated in response to a ventricular depolarization, and in response to the expiration of the escape interval, an atrial cardioversion pulse is delivered. In one embodiment of the invention, the cardioverting pulse is delivered immediately upon expiration of the derived escape interval. In a second embodiment of the invention, a ventricular pacing pulse is delivered on expiration of the escape interval, with an atrial cardioversion pulse following after a short delay.

12 Claims, 8 Drawing Sheets

METHOD AND APPARATUS FOR SYNCHRONIZATION OF ATRIAL DEFIBRILLATION PULSES

BACKGROUND OF THE INVENTION

The present invention relates to medical electrical stimulation generally, and more particularly to implantable atrial defibrillators.

Recently, there has been a renewed interest in the development of implantable atrial cardioverters and defibrillators, as the more serious consequences of persistent atrial fibrillation have come to be understood. In such devices, it is desirable to synchronize delivery of the defibrillation pulse to the ventricle to avoid triggering arrhythmias in the ventricle. This is especially so if the devices do not include the capability of performing ventricular, as well as atrial defibrillation.

A number of proposals have been set forth for controlling the timing of delivery of atrial cardioversion and defibrillation pulses. An early disclosure of an implantable atrial defibrillator, U.S. Pat. No. 3,952,750 issued to Mirowski et al., proposes simply synchronizing delivery of the atrial defibrillation pulse to a sensed R-wave. More recently, more complex systems have been proposed. For example, in PCT Patent Publication No. WO92/18198, published Oct. 29, 1992, it is proposed to sense ventricular activity at two separate locations in the ventricles, and to synchronize the delivery of atrial defibrillation pulses to the sensed ventricular depolarizations only when ventricular depolarizations are sensed at both locations within a short time interval. Alternatively, as proposed in U.S. Pat. No. 5,207,219, atrial defibrillation pulses are delivered synchronized to sensed ventricular depolarizations only when the ventricular depolarizations follow preceding ventricular depolarizations by an interval greater than a minimum V-V interval.

SUMMARY OF THE INVENTION

The present invention is directed toward a method an apparatus for controlling the timing of delivery of atrial cardioversion or defibrillation pulses. In order to determine an appropriate time for delivery of a cardioversion pulse, an apparatus according to the present invention first determines the average V-V interval associated with the ventricular rhythm in the presence of atrial fibrillation. Based upon this average interval, the apparatus calculates a shorter, derived escape interval, which is used to control timing of delivery of the atrial cardioversion or defibrillation pulse.

In a device practicing a first embodiment of the invention, the derived escape interval is used to trigger delivery of a ventricular pacing pulse or pulses to overdrive the ventricular rhythm. An atrial defibrillation or cardioversion pulse is delivered synchronized to a delivered ventricular overdrive pacing pulse. Optionally, the device may monitor the heart's response to a delivered ventricular pacing pulse, and deliver a synchronized atrial defibrillation or cardioversion pulse only if the ventricular pacing pulse is determined to be successful in triggering a ventricular depolarization.

In a device practicing a second embodiment of the device, the derived escape interval is used to set the delivery time of the atrial cardioversion or defibrillation pulse, such that in the absence of a sensed ventricular depolarization prior to expiration of the derived escape interval, an atrial cardioversion or defibrillation pulse will be delivered at the expiration of the derived escape interval. In both embodiments, the derived escape interval must be greater than a predetermined minimum interval, in order to avoid delivery of atrial cardioversion or defibrillation pulses too closely timed to preceding ventricular depolarizations.

DETAILED DESCRIPTION OF THE PREFERRED EMBODIMENT

Figure 1:
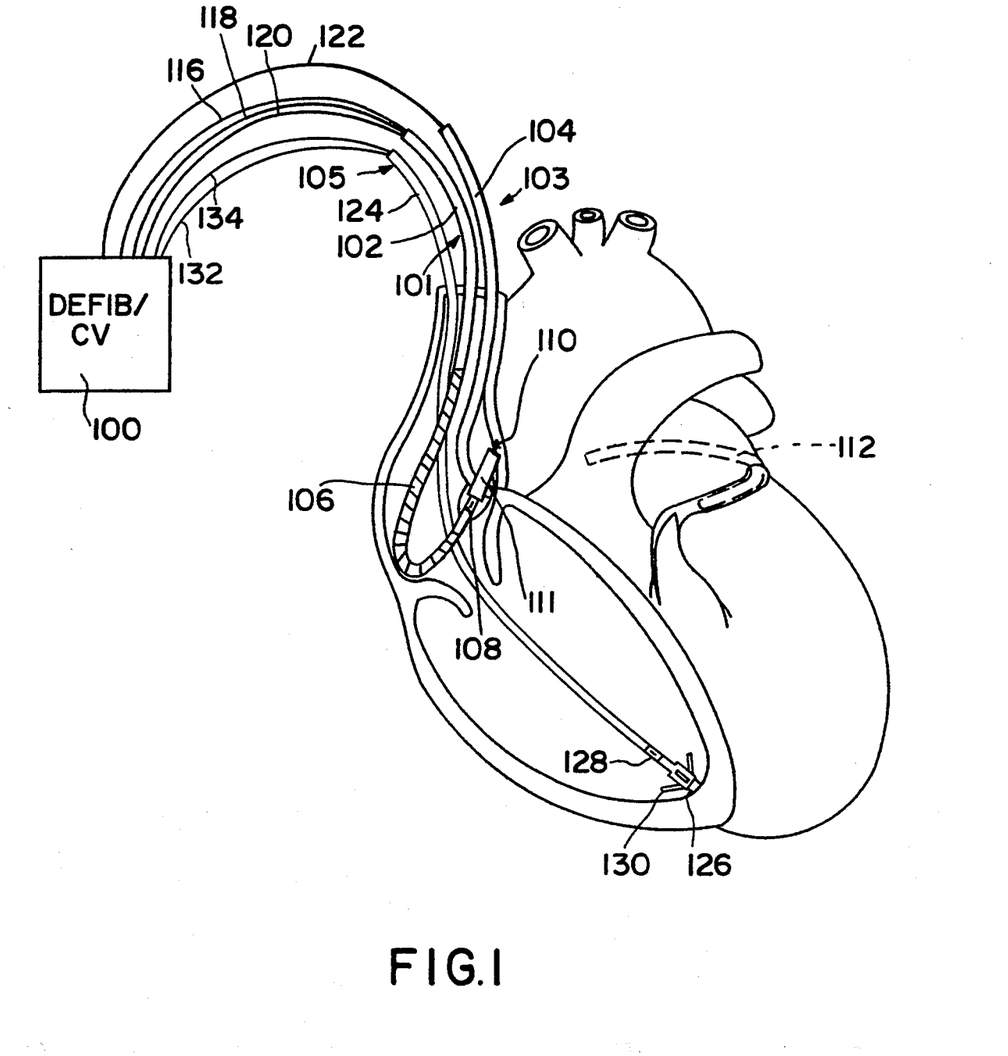
FIG. 1 illustrates a implantable defibrillator and lead set in which the present invention may be embodied.

FIG. 1 is a cutaway view of the human heart in which a lead system suitable for use in practicing the present invention has been implanted. The lead system includes three leads. A right atrial lead 101 includes an elongated insulative lead body 102, to which a coiled defibrillation electrode 106 has been mounted. The distal end of the lead includes an electrode head 111, carrying a helical electrode 110 and a ring electrode 108. The electrodes 106, 108 and 110 are coupled to an implantable pacemaker/cardioverter/defibrillator 100 by means of conductors 116, 118 and 120. Electrodes 108 and 110 are employed for cardiac pacing and sensing in the atrium.

A coronary sinus lead 103 also has an elongated insulative lead body 104 which carries a coiled defibrillation electrode at its distal end, located as generally indicated in broken outline at 112. Electrode 112 is located within the coronary sinus and the great cardiac vein. Preferably the proximal end of the electrode 112 is spaced about 3 to 8 cm from the opening of the coronary sinus into the right atrium. Electrode 112 is coupled to implantable pacemaker/cardioverter/defibrillator 100 by means of conductor 122.

A right ventricular pacing lead 105 also includes an elongated insulative lead body 124. The distal end of the lead 105 carries a tip electrode 126 and a ring electrode 128. The electrodes 126 and 128 are coupled to implantable pacemaker/cardioverter/defibrillator 100 by means of conductors 132 and 134. Electrodes 126 and 128 are used for cardiac pacing and sensing in the ventricle. Tines 130 anchor the distal end of the lead in the right ventricular apex. An additional electrode may be located on the housing of the device 100 and may be employed to accomplish pacing and sensing functions in conjunction with the other illustrated pacing and sensing electrodes. Although not illustrated, lead 124 may include an additional defibrillation electrode for location in the right ventricle. This ventricular defibrillation electrode may also be employed for atrial defibrillation. If the invention is embodied in a device capable of detecting ventricular tachyarrhythmias, such a ventricular defibrillation electrode would also be used for ventricular cardioversion and defibrillation.

Electrodes 108 and 110, and optionally electrodes 126 and 128 are used by pacemaker/cardioverter/defibrillator 100 to sense the electrical activity of the atrium and optionally the ventricle to diagnose the presence of atrial tachycardias or fibrillation requiring delivery of high voltage cardioversion or defibrillation pulses, respectively. In response to the detection of tachycardia or fibrillation, pacemaker/cardioverter/defibrillator 100 generates a high voltage pulse between electrodes 106 and 112. Electrodes 108, 110, 126 and 128, along with an electrode located on the housing of the device 100, may also be employed in order to deliver any of the various conventional pacing therapies, including pacing in single chamber (VVI, AII, etc.) modes or dual chamber (VDD, DVI, DDD, DDI, etc) modes.

In the embodiments disclosed in detail below, the pacemaker/ cardioverter/defibrillator 100 operates in VVI pacing mode, using electrode 126 and an electrode mounted on the housing of the device for delivery of cardiac pacing pulses. Electrodes 128 and 126 are employed for sensing during VVI pacing. Electrode 128 and an electrode on the device housing may be employed for capture detection following delivery of overdrive pacing pulses during the synchronization sequence. The electrode on the housing may take the form of some or all of a conductive housing. Electrodes 108 and 110 are employed for atrial tachyarrhythmia detection and may be employed for atrial sensing and pacing if a dual-chamber pacing mode is desired.

Figure 2:
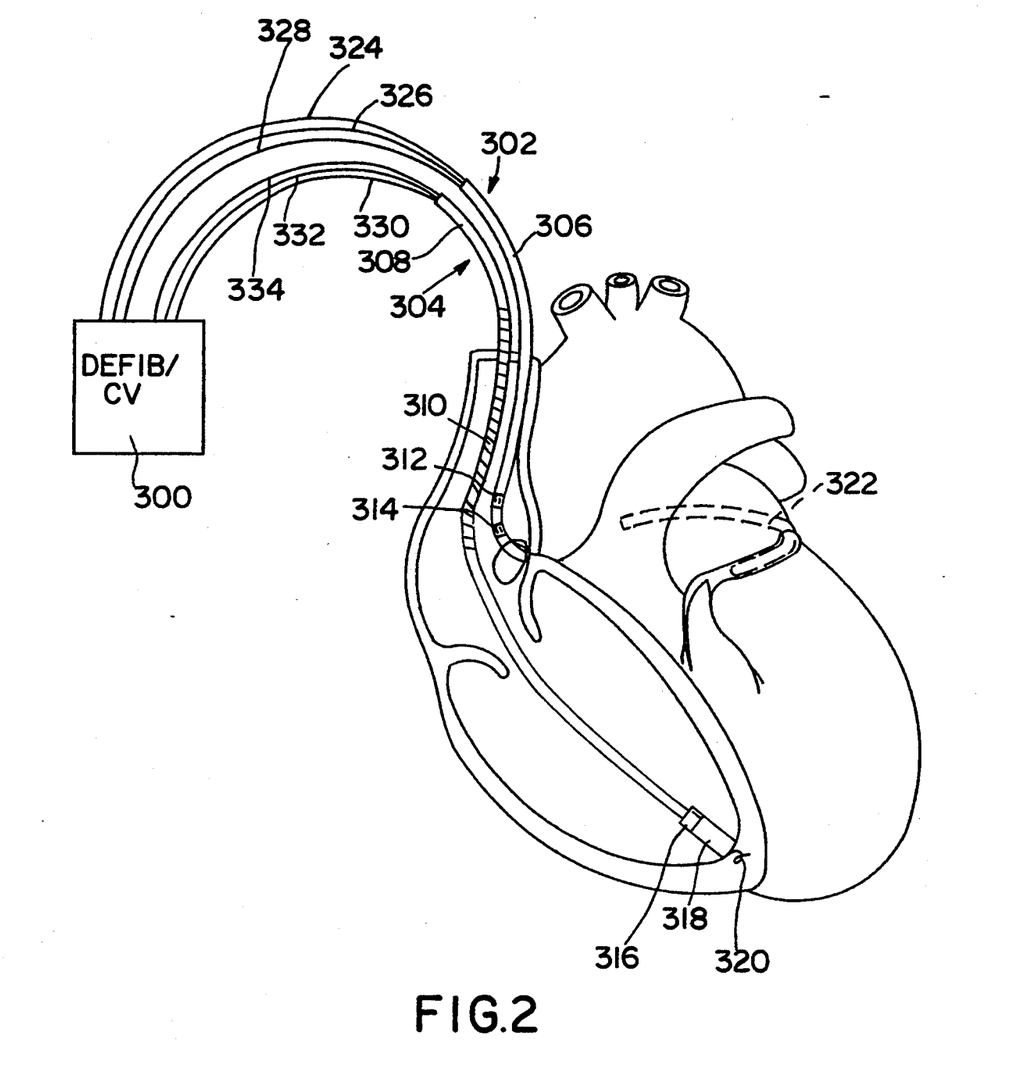
FIG. 2 illustrates an implantable defibrillator and an alternate lead set in which the present invention may be embodied.

FIG. 2 illustrates a cardioverter/defibrillator 300 in conjunction with an alternative lead set to that illustrated in FIG. 1. This lead set differs from that illustrated in FIG. 1 in that it includes only two leads, simplifying the implant procedure. A coronary sinus lead 302 is provided, which corresponds generally to coronary sinus lead 103 in FIG. 1, with the exception that it is provided with two additional ring electrodes 312 and 314, located in the right atrium of the heart. Like lead 103, lead 302 is provided with an elongated insulative lead body 306 which carries an elongated defibrillation electrode 322. Three conductors, 324, 326 and 328 are located within lead body 306, and couple electrodes 312, 314 and 322 to defibrillator cardioverter 300.

Lead 304 corresponds generally to lead 101, as illustrated in FIG. 1, with the exception that it is not preformed into a J-shaped curve at its distal end and in that the defibrillation electrode 310 is located in a more proximal position, such that when the electrode head 318, carrying ring electrode 316 and helical electrode 320 is located in the ventricular apex, defibrillation electrode 310 is located in the superior vena cava and/or right atrium. Mounted within insulative lead body 308 of lead 304 are conductors 330, 332 and 334 which serve to couple electrodes 310, 316 and 320 to pacemaker/cardioverter/defibrillator 300. An electrode may also be mounted on the housing of the pacemaker/cardioverter/defibrillator 300.

Electrodes 312 and 314 are employed for sensing atrial depolarizations to diagnose the existence of atrial tachycardias or fibrillation or in conjunction with atrial synchronized ventricular pacing modes, such as VVD pacing. Electrodes 316 and 320 may be used for performing cardiac pacing and sensing functions in the ventricle, and may be used in conjunction with electrodes 312 and 314 for diagnosing the existence of atrial tachycardias and/or fibrillation, requiring delivery of high voltage cardioversion or defibrillation shocks via electrodes 310 and 322.

Figure 3:
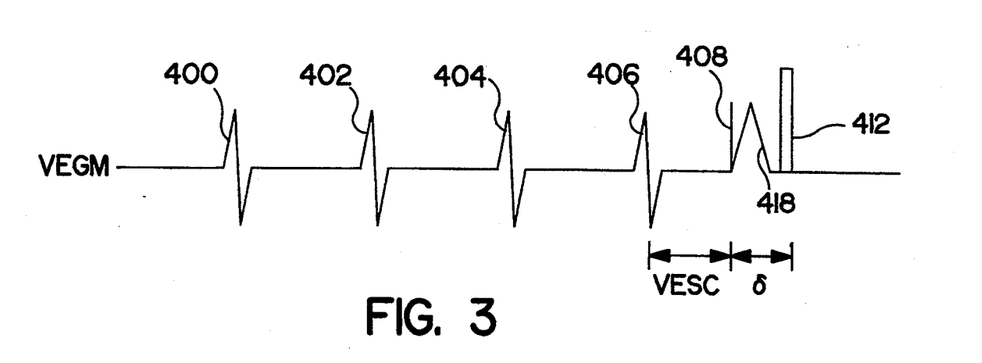
FIG. 3 is a simulated set of electrograms illustrating the operation of a first embodiment of the invention.

FIG. 3 is a simulated ventricular electrogram illustrating the synchronization of an atrial cardioversion or defibrillation pulse according to a first embodiment of the present invention. In reviewing these electrograms, it should be understood that the apparatus is simultaneously sensing the atrial electrogram, not visible in these figures, for purposes of determining whether atrial tachycardias or fibrillation requiring delivery of high energy cardioversion or defibrillation pulse are present. The sensed ventricular electrogram may also be employed in conjunction with this diagnostic function. In any case, the device monitors and stores the detected intervals between sensed heart events, including intervals between successive R-waves (V-V intervals), intervals between successive P-waves (A-A intervals) and intervals between successive R and P waves (A-V and VA intervals). Based upon these stored intervals, a determination is made as to whether or not an atrial arrhythmia requiring delivery of a cardioversion or defibrillation pulse is present. If so, synchronization and delivery of an atrial cardioversion or defibrillation pulse according to the present invention is attempted.

In FIG. 3, R-waves 400, 402, 404 and 406 are illustrated. For purposes of understanding the electrogram, it should be understood that at some point between sensing of R-wave 404 and R-wave 406, the device has finished charging high voltage capacitors used for generation of cardioversion and defibrillation pulses, following a determination that an atrial arrhythmia requiring delivery of a high energy cardioversion or defibrillation pulse is present. Preferably the device continues to sense in the atrium and ventricles during charging, and aborts charging if the sensed arrhythmia spontaneously terminates. Following charge-up, the device allows the ventricular escape interval initiated at R-wave 404 to time out until it is reset by R-wave 406. The device then determines the average interval separating R-waves 400, 402, 404 and 406, calculating a new, shorter derived escape interval as illustrated, labelled VESC. If a ventricular depolarization is sensed prior to expiration of VESC, a new value of VESC is calculated and a subsequent attempt to synchronize is made. In the absence of sensing of further ventricular activity prior to the expiration of the VESC interval, a ventricular pacing pulse 408 is generated. The device checks thereafter to determine whether the pacing pulse has been successful in capturing the ventricle, as indicated by paced R-wave 410. Because pacing pulse 408 was successful in capturing the ventricle, atrial cardioversion or defibrillation pulse 412 is delivered thereafter, following a delay "δ" initiated at delivery of the pacing pulse 408. The value of δ, for example, may be 20–100 milliseconds. If the ventricular pacing pulse is ineffective to capture the ventricle, it may be incremented and a subsequent synchronization attempt undertaken.

As part of the process of defining the duration of VESC, the device compares VESC to a minimum interval to determine whether delivery of a ventricular pacing pulse at the expiration of VESC would produce an R-R interval which is too short for safe synchronization of the atrial defibrillation pulse. The duration of this minimum interval may be, for example 200 ms to 350 ms. If VESC is less than the minimum interval, the overdrive pacing pulse is not delivered and correspondingly no atrial cardioversion or defibrillation pulse is delivered. The cardioversion or defibrillation therapy may be immediately aborted and the fibrillation detection function reset, so that if the fibrillation persists, a subsequent attempt to deliver a synchronized pulse will be made. Alternatively, a number of attempts to derive an appropriate VESC value may be made before aborting the cardioversion or defibrillation therapy.

Figure 4:
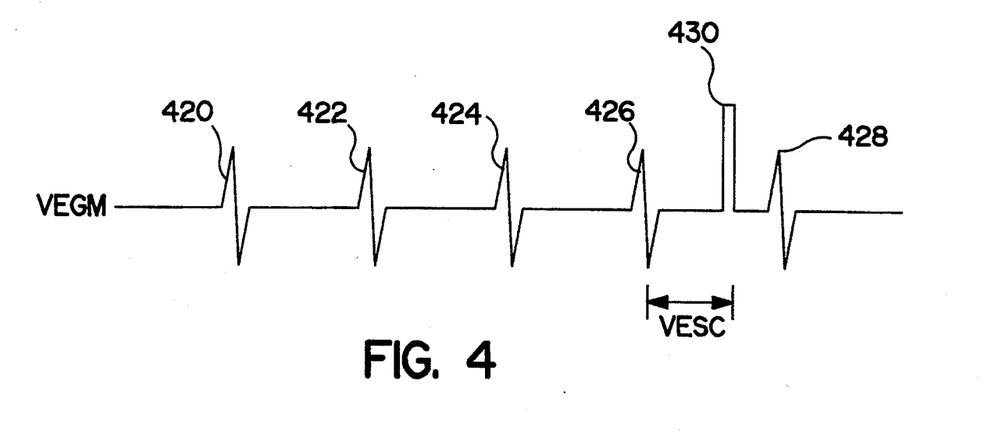
FIG. 4 is a simulated set of electrograms illustrating the operation of a second embodiment of the invention.

FIG. 4 illustrates an alternative synchronization methodology, according to the present invention. R-waves 420, 422, 424, 426 and 428 are illustrated, indicating the ventricular rhythm in the presence of atrial fibrillation. Similar to FIG. 3 discussed above, it should be understood that between R-waves 424 and 426, the apparatus has completed charging of its high voltage output capacitors. The ventricular escape interval presently in process is allowed to time out until reset by R-wave 426. The intervals separating R-waves 420, 422, 424 and 426 are used to derive an average interval value, from which a new, shorter, escape interval VESC is derived, as described above in conjunction with FIG. 3. However, in the embodiment illustrated in FIG. 4, a high energy cardioversion or defibrillation pulse 430 is simply delivered at the expiration of VESC, rather than triggering delivery of ventricular pacing pulse, provided that no intervening R-waves are sensed. In the event that an R-wave is sensed prior to the expiration of the VESC, as in the case of the embodiment illustrated in FIG. 3, the average R-R interval is updated, a new value for VESC is derived, and a subsequent attempt at synchronization is made.

Figure 5:
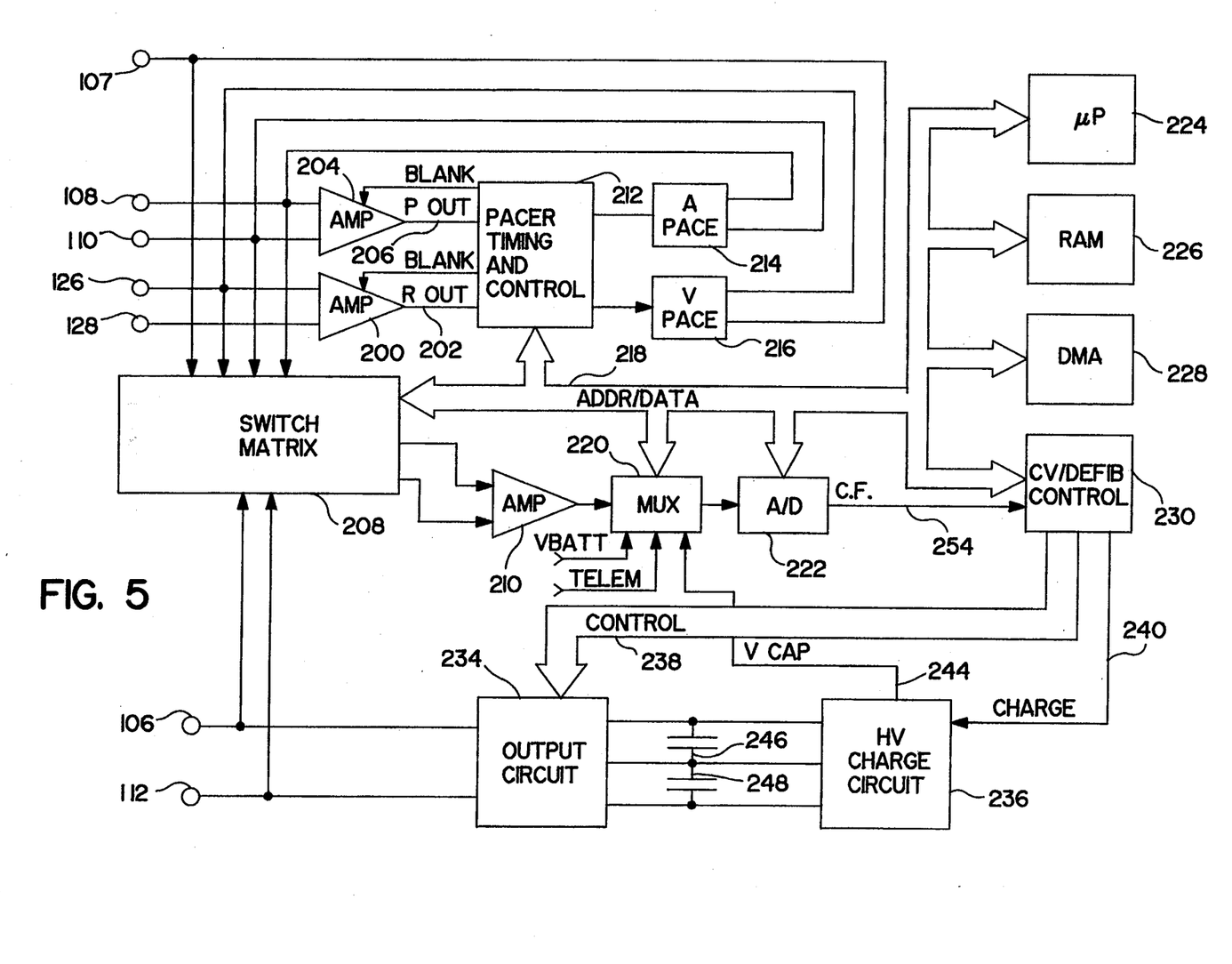
FIG. 5 is a functional schematic diagram of an implantable pacemaker/cardioverter/defibrillator in which the invention may be embodied.

FIG. 5 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including cardioverter and defibrillators which do not provide anti-tachycardia pacing therapies.

The device is provided with an electrode system including electrodes as illustrated in FIG. 1, with the addition of electrode 107, located on the housing of the implanted device. Electrode 112 is a defibrillation electrode located in the coronary sinus and great vein. Electrode 106 is a defibrillation electrode located in the right atrium and/or the superior vena cava. Both electrodes 112 and 106 are coupled to high voltage output circuit 234. Electrodes 128 and 126 are located on or in the right ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 126 and 128 exceeds the present sensing threshold.

Electrodes 108 and 110 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 108 and 110 exceeds the present sensing threshold. The general operation of the R-wave and P-wave amplifiers 200 and 204 may correspond to that disclosed in allowed, commonly assigned, co-pending U.S. Pat. No. 5,117,824, by Keimel, et al., for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Switch matrix 208 is also used to select electrodes for use in performing the capture detection function following delivery of overdrive ventricular pacing pulses during the synchronization sequence. For example, electrode 128 and electrode 107 located on the housing of the device may be so employed. Other electrode configurations are also easily selected. The signal from wide band amplifier 210, as digitized by A/D converter 222 may be stored and analyzed by microprocessor 224 during the delay period δ.

Capture detection may be accomplished using any of the various capture detection methods known to the art. As illustrated, capture detection is accomplished by means of a pair of sensing electrodes which do not include the pacing cathode 126 and by monitoring the EGM following delivery of the pacing pulse to determine whether a depolarization follows, as disclosed in U.S. Pat. No. 4,969,464, issued to Callahan et al. and incorporated herein by reference in its entirety. However capture detection by means of a sensor responsive to physical contraction of the heart, such as a pressure or impedance sensor may also usefully be employed. Alternatively, the same electrodes may be used for pacing and capture detection provided that a method of rapidly discharging the residual polarization on the pacing electrodes is provided as disclosed in allowed U.S. patent application Ser. No. 07/626,061 filed Dec. 12, 1990 by Hudrlik for "Electronic Capture Detection for a Pacer", incorporated herein by reference in its entirety.

The remainder of the circuitry is dedicated to the provision of cardiac pacing, cardioversion and defibrillation therapies, and, for purposes of the present invention may correspond to circuitry known in the prior art. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with antitachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by a signals on lines 202 and 206, and in accordance with the selected mode of pacing on timeout trigger generation of pacing pulses by pacer output circuitry 214 and 216, which are coupled to electrodes 126 and 107, for ventricular pacing and to electrodes 108 and 110 for atrial pacing. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, and is awakened by interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting an atrial tachyarrhythmia.

Detection of atrial tachyarrhythmias, as employed in the present invention, may correspond to tachyarrhythmia detection algorithms known to the art. For example, presence of atrial tachyarrhythmia may be confirmed by means of detection of a sustained series of short P-P intervals of an average rate indicative of tachyarrhythmia or an unbroken series of short P-P intervals. The suddenness of onset of the detected high rates, the stability of the high rates, or a number of other factors known to the art may also be measured at this time. Appropriate detection methodologies measuring such factors are described in U.S. Pat. No. 4,726,380, issued to Vollmann, U.S. Pat. No. 4,880,005, issued to Pless et al and U.S. Pat. No. 4,830,006, issued to Haluska et al. Alternatively, the tachyarrhythmia analysis and recognition methodology disclosed in the article "Automatic Tachycardia Recognition" by Arzbaecher et al., published in *Pace*, May-June, 1984, pp. 541–547. However, one of the advantages of the present invention is that it is believed practicable in conjunction with all prior art atrial tachycardia detection algorithms.

The device also detects termination of atrial tachyarrhythmias, for example by detection of a sequence sequential P-P intervals greater than a preset duration, or by detection of a average atrial rate, over a series of Pwaves, which is less than a preset value. Detection of termination is preferably operative during charging of the high voltage output capacitors 246 and 248, as well as during the cardioversion or defibrillation synchronization sequence according to the present invention.

In the event that an atrial tachyarrhythmia is detected, and an antitachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of antitachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the counters in circuitry 212 to control timing of such cardioversion and defibrillation pulses, as well as associated refractory periods. In response to the detection of an atrial tachyarrhythmia requiring a cardioversion or defibrillation pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to pacing and awaits the next successive interrupt due to pacing or the occurrence of a sensed atrial or ventricular depolarization.

Figure 6:
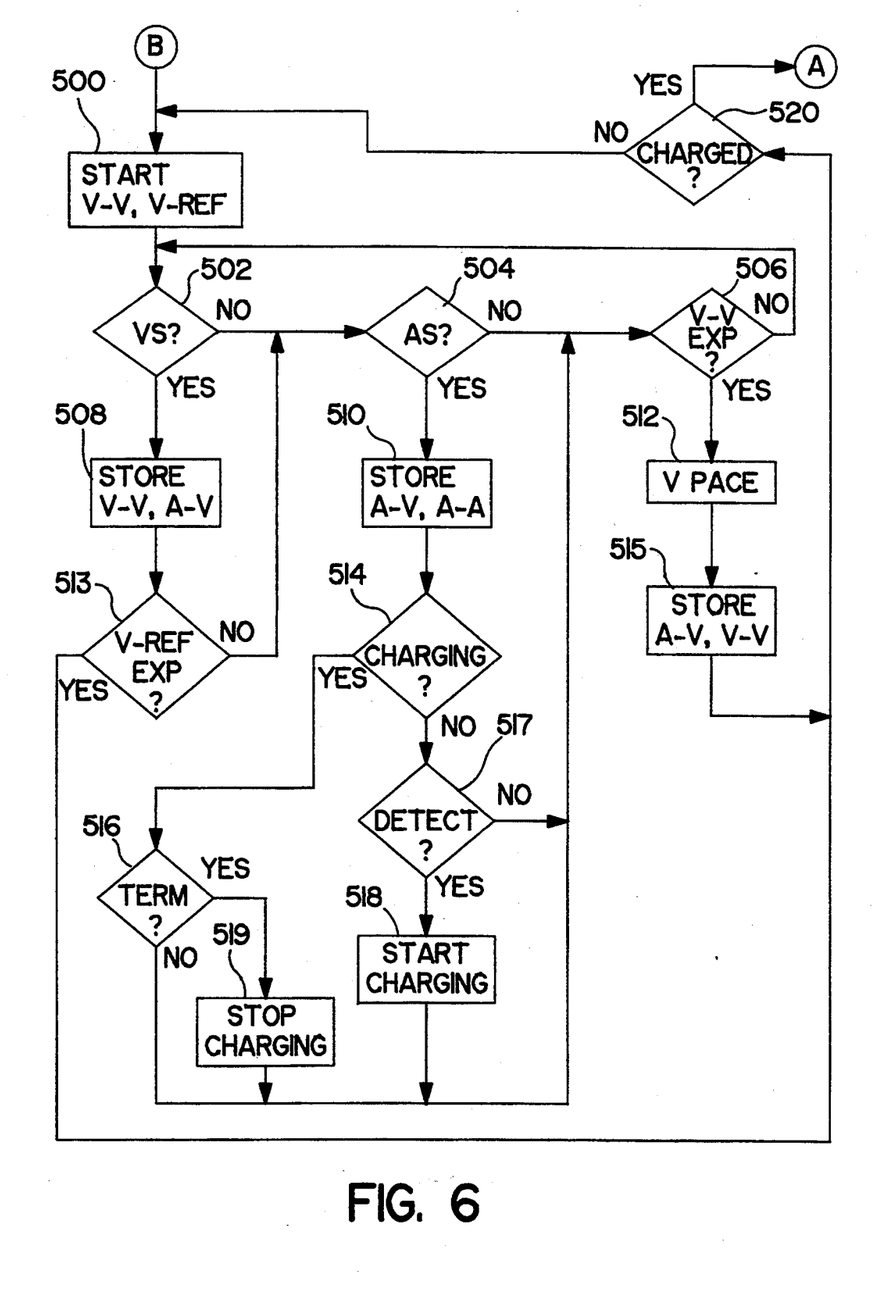
FIG. 6 is a functional flow chart illustrating the general operation of a pacemaker/cardioverter/defibrillator embodying the invention.

FIG. 6 is a functional flowchart illustrating the overall operation of the device according to the present invention, while pacing in the VVI mode, prior to detection of atrial tachycardia or fibrillation. In the embodiment described, anti-tachycardia pacing is not provided. However, the present invention may be employed in devices which do provide anti-tachycardia pacing in either or both chambers of the heart. The flowchart may be entered at 500, immediately following sensing of a ventricular depolarization or delivery of a ventricular pacing pulse. At this point, the apparatus initiates timing of the V-V escape interval and the ventricular refractory interval. The V-V escape interval defines the basic pacing interval of the device, which is the interval following a non-refractory sensed ventricular depolarization or delivered pacing pulse and the next subsequent delivered ventricular pacing pulse, in the absence of non-refractory sensed ventricular depolarizations in the interim. The ventricular refractory interval is an interval following sensing or pacing in the ventricle during which a sensed ventricular depolarization will not restart the V-V interval.

The device then awaits the occurrence of a sensed ventricular sense depolarization at 502, the occurrence of a sensed atrial depolarization at 504, or expiration of the V-V escape interval at 506. On expiration of the V-V escape interval, a ventricular pacing pulse is delivered at 512, and the A-V and V-V intervals ending with the delivery of the ventricular pacing pulse are stored for use in arrhythmia detection and analysis. The device then checks at 520 to determine whether the high voltage output capacitors are fully charged, which would indicate prior detection of atrial fibrillation and the readiness of the device to deliver a cardioversion or defibrillation pulse. If the capacitors are not fully charged, the ventricular pacing cycle is restarted at 500.

If a ventricular depolarization is sensed at 502, the device stores the V-V and A-V intervals ending with the sensed depolarization at 508 for use in arrhythmia detection and analysis. The device then checks to determine whether the ventricular refractory period has expired at 513. If the ventricular refractory period has expired, the device checks at 520 to determine whether it is ready to delivery an atrial defibrillation or cardioversion pulse at 520, and if not, restarts the ventricular pacing cycle at 500.

In the absence of a non-refractory sensed depolarization, the device checks for an atrial depolarization at 504. If an atrial depolarization is sensed, the V-A and A-A intervals ending with the sensed atrial depolarization are stored at 510. The device then checks at 514 to determine whether atrial fibrillation or tachycardia requiring delivery of a high voltage pulse has previously been detected, such that the high voltage capacitors are charging. If fibrillation or such a tachyarrhythmia has not been previously detected, the device checks at 517 to determine whether the preceding series of stored A-A, V-V, A-V and V-A intervals together define an atrial tachyarrhythmia which requires delivery of a high voltage cardioversion or defibrillation pulse. If so, the device initiates capacitor charging at 518, and the device continues to await expiration of the V-V interval at 506, atrial sensing at 504 or ventricular sensing at 502.

In the event that tachycardia or fibrillation has previously been detected and thus the capacitors are in the process of charging at 514, the device checks at 516 to determine whether the preceding series of stored AV, V-A, A-A and V-V intervals indicates termination of the previously detected atrial arrhythmia. If the arrhythmia has terminated, charging is stopped a 519. If the arrhythmia is still in process, the device continues to await expiration of the V-V escape interval at 506, atrial sensing at 504, or ventricular sensing at 502.

Figure 7:
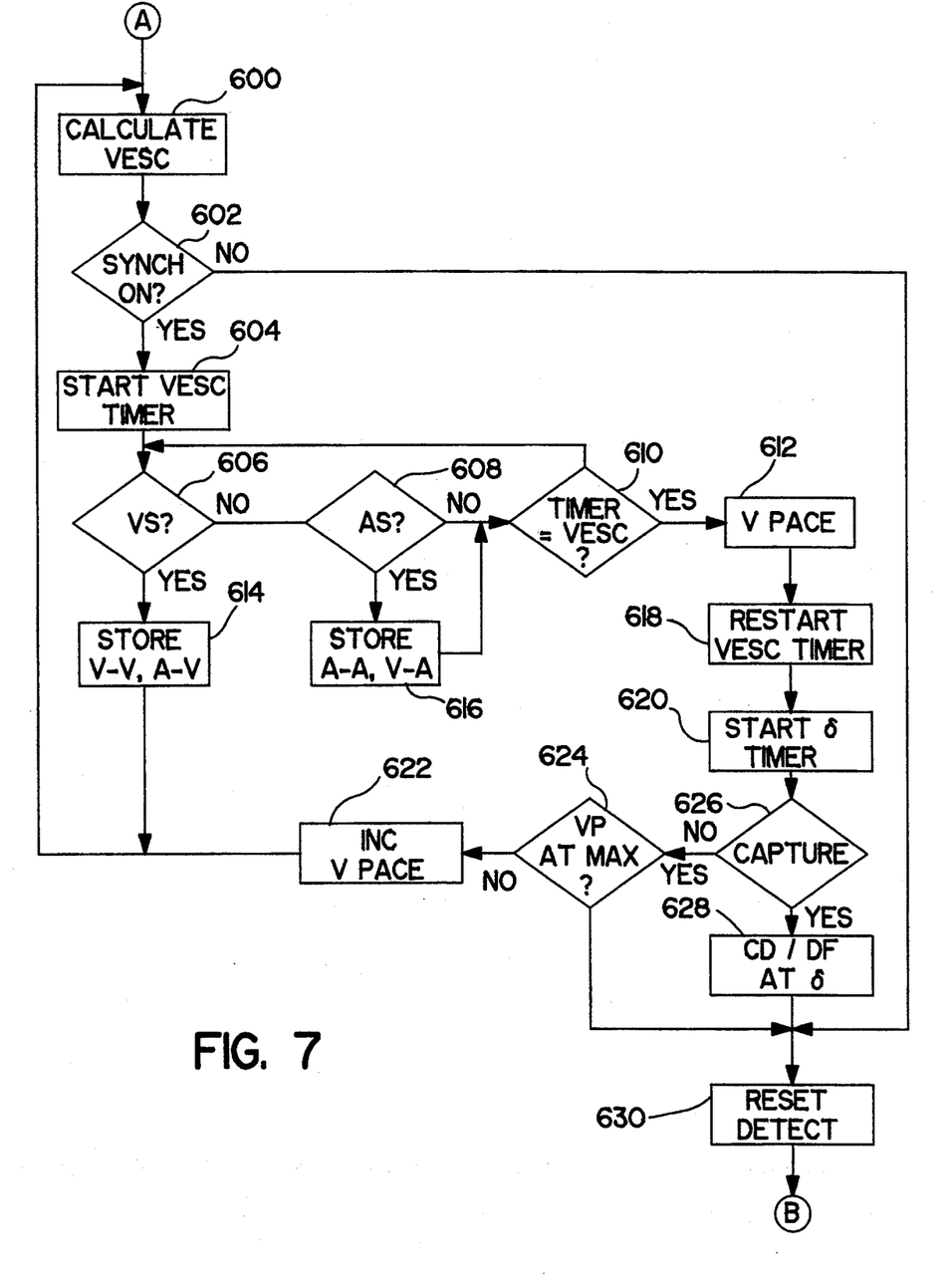
FIG. 7 is a functional flow chart illustrating the operation of a first embodiment of the invention to synchronize delivery of an atrial defibrillation pulse, corresponding to the operation illustrated in FIG. 3.
Figure 8:
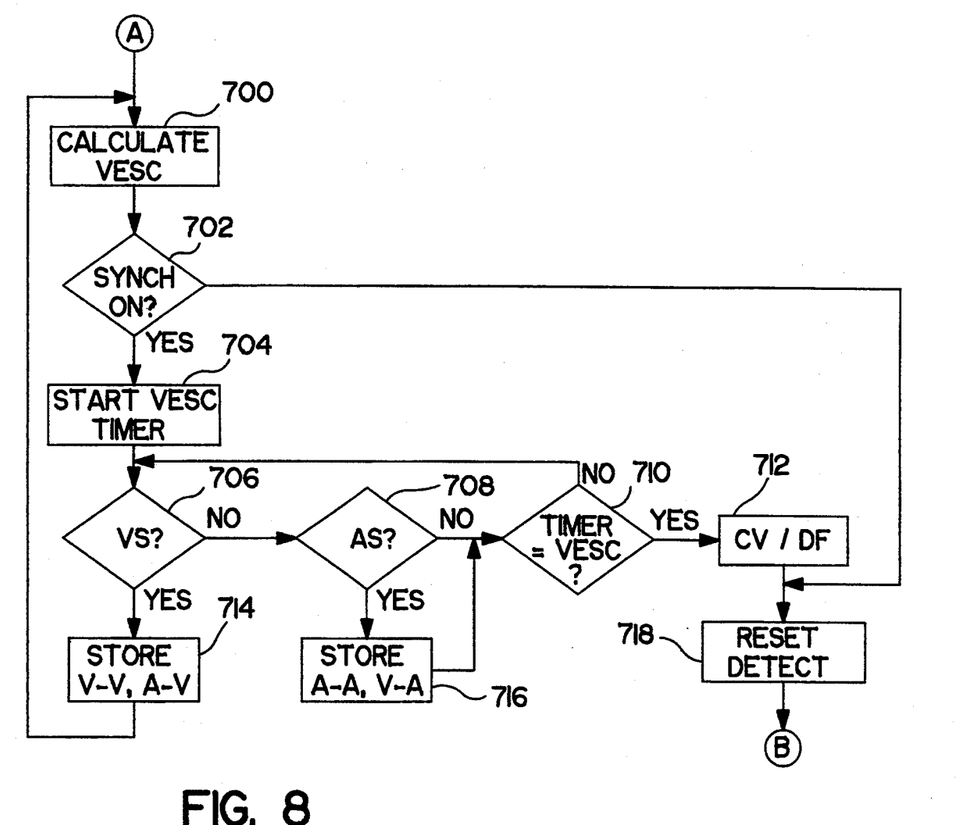
FIG. 8 is a functional flow chart illustrating the operation of a second embodiment of the invention to synchronize delivery of an atrial defibrillation pulse, corresponding to the operation illustrated in FIG. 4.

Assuming that an atrial tachycardia or fibrillation has been detected, following the next subsequent expiration of the V-V escape interval at 506 or non-refractory sensed depolarization at 513, the device will check at 520 to determine whether the high voltage capacitors are charged, and will determine that the capacitors are charged, and the device is ready to deliver an atrial cardioversion or defibrillation pulse. At this point, an attempt to deliver an atrial cardioversion or defibrillation pulse synchronized according to the present invention is undertaken. FIGS. 7 and 8 and illustrate alternative synchronization procedures, according to the present invention.

In FIG. 7, the synchronization procedure is initiated at 600 by calculation of the derived escape interval VESC, discussed above. The specific details of calculation of VESC are set forth in FIG. 9 below. As part of the calculation procedure, a determination is made as to whether delivery of a synchronized atrial cardioversion pulse is appropriate. At 602, the device checks to determine whether delivery of a synchronized cardioversion pulse is appropriate. If not, the atrial tachycardia and fibrillation detection process is reset at 630, and the device awaits subsequent re-detection of atrial fibrillation or tachycardia. If, however, delivery of a synchronized cardioversion or defibrillation pulse is appropriate, the device activates the VESC timer, which may be a timer in circuitry 212 which counts to a predetermined value, corresponding to VESC. While the VESC timer is running, the device checks at 606 to determine whether ventricular depolarizations are sensed, optionally checks at 608 to determine whether atrial depolarizations are sensed, and checks at 610 for the timer reaching a count equal to VESC. If a ventricular depolarization is sensed before the timer reaches VESC, the V-V and A-V intervals ended by the sensed depolarization are stored at 614, and a new value of VESC is calculated at 600. If atrial depolarizations are sensed 608, prior to the timer equalling VESC, the A-A and V-A intervals ended by the sensed atrial depolarization are optionally stored at 616 for later diagnostic use.

If the count of the VESC timer equals VESC at 610, a ventricular overdrive pacing pulse is delivered at 612. The VESC timer is restarted at 618, and a timer in circuitry 212 defining the delay interval 3, discussed above, is initialized at 620. The device checks at 626 to determine whether the ventricular pacing pulse delivered at 612 has captured the heart. If not, the device optionally checks at 624 to determine whether the parameters of the ventricular pacing pulse are set at their maximum amplitude and duration at 624. If they are not set at the maximum amplitude and duration, these values are incremented at 622, and a new value of VESC is calculated at 600, triggering a new synchronization cycle. Alternatively, in response to a failure to capture the ventricle, the device may abort the therapy or alternatively simply proceed directly to recalculate a new VESC value at 600. The VESC timer, previously started, will be monitored to determine when it reaches the new value of VESC at 610.

If capture is accomplished, a cardioversion or defibrillation pulse is delivered at 628, following expiration of the delay period δ. The fibrillation and tachycardia detection criteria are reset at 630, and the device awaits subsequent re-detection of atrial tachycardia or fibrillation, while returning to VVI pacing mode at 500 (FIG. 6).

FIG. 8 describes a simpler, alternative synchronization process which may be substituted for the synchronization process of FIG. 7. Like the process illustrated in FIG. 7, the device begins the synchronization process by calculating the value of VESC at 700, determining whether synchronization is appropriate at 702, starting the VESC timer at 704, and awaiting ventricular sensing at 706, atrial sensing at 708 or expiration of the VESC timer at 710. Sensed atrial and ventricular depolarizations are stored at 714 and 71 6, with sensed ventricular depolarizations triggering calculation of a new of VESC at 700, and a subsequent synchronization cycle.

The operation of the synchronization process illustrated in FIG. 8 differs in that on expiration of the VESC integral at 710, a cardioversion or defibrillation pulse is immediately generated at 712, following reset of the fibrillation and tachycardia detection criteria at 718, and return of the device to VVI pacing mode at 500, awaiting subsequent detection of fibrillation or tachycardia.

Figure 9:
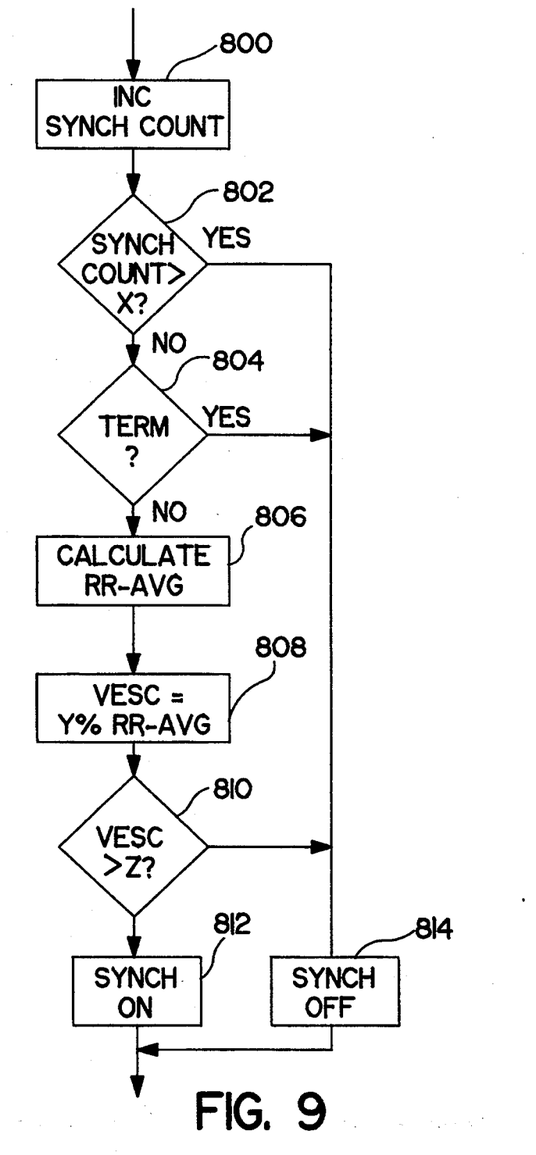
FIG. 9 is a functional flow chart illustrating the operation of a portion of the flow charts of FIGS. 7 and 8 in more detail.

FIG. 9 illustrates the details of the method by which a device according to the present invention calculates the derived escape interval VESC, and determine whether a subsequent synchronization cycle is appropriate. The functional flowchart of FIG. 9 corresponds to box 600 of FIG. 7 and to box 700 of FIG. 8. At 800, a synchronization count is incremented. This count keeps track of the number of times that a new value of VESC has been calculated, following charge up of the high voltage output capacitors. At 802, the device checks to determine whether the number of synchronization attempts exceeds a maximum acceptable value "X". If the number of attempts exceeds the maximum acceptable value X, the synchronization function is set off at 814. As a result, at 602 (FIG. 7) or 702 (FIG. 8), the device will determine that synchronization is inappropriate, and will proceed to directly to reset tachycardia and fibrillation detection criteria and will return to VVI pacing at 500 (FIG. 6).

Assuming that the synchronization count is less than the maximum allowed value, the device checks at 804 to determine whether the stored A-V, V-A, A-A and V-V intervals during the last synchronization sequence indicate termination of the detected arrhythmia. If so, synchronization is set off at 814, with consequences as discussed above. If termination is not detected, the preceding series of stored V-V intervals is employed to calculate an average interval between successive R-wave at 806, and VESC is derived by taking a predetermined percentage "Y" of the average V-V interval at 808. The value of VESC is compared to a minimum interval value "Z" at 810. If the value of VESC is less than the minimum interval Z, the synchronization function is set off at 814, with consequences as discussed above. If the value of VESC is greater than the minimum interval "Z", synchronization is set on at 812, allowing a subsequent attempt to deliver a synchronized atrial cardioversion or defibrillation pulse.

The functions illustrated in FIG. 9 serve to derive an appropriate time for delivery of an atrial cardioversion or defibrillation pulse. They serve as well to prevent inappropriate delivery of an atrial cardioversion or defibrillation pulse in those circumstances in which synchronization is not possible, or in which synchronization would produce too short an interval between a ventricular depolarization and delivery of an atrial cardioversion or defibrillation pulse.

In conjunction with the above specification, I claim:

1. An atrial cardioverter or defibrillator, comprising:
   means for detecting a tachyarrhythmia in a patient's atrium;
   means for delivering a cardioversion or defibrillation pulse to said patient's atrium; and
   synchronization means for triggering delivery of said cardioversion or defibrillation pulse, said synchronization means comprising:
   means for sensing depolarizations of said patient's ventricle;
   means for measuring intervals between sensed ventricular depolarizations to derive an interval indicative of intrinsic heart rate;
   means for deriving an escape interval less than said interval indicative of intrinsic heart rate, initiated on a sensed ventricular depolarization; and
   means for triggering delivery of said cardioversion or defibrillation pulse in response to expiration of said escape interval, in the absence of sensed ventricular depolarizations during said escape interval.

2. An atrial cardioverter or defibrillator, comprising:
   means for detecting a tachyarrhythmia in a patient's atrium;
   means for delivering a cardioversion or defibrillation pulse to said patient's atrium; and
   synchronization means for triggering delivery of said cardioversion or defibrillation pulse, said synchronization means comprising:
   means for sensing depolarizations of said patient's ventricle;
   means for measuring intervals between sensed ventricular depolarizations to determine an interval indicative of intrinsic heart rate;
   means for defining a single escape interval less than said interval indicative of intrinsic heart rate, initiated on a said sensed ventricular depolarization; and
   means for triggering delivery of said cardioversion or defibrillation pulse in response to expiration of said single escape interval, in the absence of sensed ventricular depolarizations during said single escape interval.

3. An atrial cardioverter or defibrillator according to claim 1 or claim 2, wherein said triggering means comprises means for triggering delivery of said cardioversion or defibrillation pulse on expiration of said escape interval, in the absence of sensed ventricular depolarizations during said escape interval.

4. An atrial cardioverter or defibrillator comprising:
   means for detecting a tachyarrhythmia in a patient's atrium;
   means for delivering a cardioversion or defibrillation pulse to said patient's atrium; and
   synchronization means for triggering delivery of said cardioversion or defibrillation pulse, said synchronization means comprising:
   means for sensing depolarizations of said patient's ventricle;
   means for measuring intervals between sensed ventricular depolarizations;

means for deriving an escape interval initiated on a sensed ventricular depolarization, based upon measured intervals between sensed ventricular depolarizations;

means for triggering delivery of said cardioversion or defibrillation pulse in response to expiration of said escape interval, in the absence of sensed ventricular depolarizations during said escape interval; and means for delivering a pacing pulse to said patient's ventricle on expiration of said escape interval, in the absence of sensed ventricular depolarizations during said escape interval, and wherein said triggering means comprises means for triggering delivery of said cardioversion or defibrillation pulse on expiration of a delay interval following expiration of said escape interval.

5. An atrial cardioverter or defibrillator according to claim 4, further comprising capture detection means for determining whether said delivered pacing pulse caused a depolarization of said patient's ventricle and wherein said triggering means comprises means responsive to said capture detection means for preventing delivery of said cardioversion or defibrillation pulse if said pacing pulse does not cause a ventricular depolarization.

6. An atrial cardioverter or defibrillator, comprising:
means for detecting a tachyarrhythmia in a patient's atrium;
means for delivering a cardioversion or defibrillation pulse to said patient's atrium; and
synchronization means for triggering delivery of said cardioversion or defibrillation pulse, said synchronization means comprising:
means for sensing depolarizations of said patient's ventricle;
means for measuring intervals between sensed ventricular depolarizations;
means for deriving an escape interval initiated on a sensed ventricular depolarization, based upon measured intervals between sensed ventricular depolarizations; and
means for triggering delivery of said cardioversion or defibrillation pulse in response to expiration of said escape interval, in the absence of sensed ventricular depolarizations during said escape interval; and
wherein said deriving means comprises means for determining whether said derived escape interval is less than a minimum interval, and means for preventing delivery of said cardioversion or defibrillation pulse if said derived interval is less than said minimum interval.

7. A method of atrial cardioversion or defibrillation, comprising:
detecting a tachyarrhythmia in a patient's atrium;
sensing depolarizations of said patient's ventricle;
measuring intervals between sensed ventricular depolarizations to derive an interval indicative of intrinsic heart rate;
deriving an escape interval less than said interval indicative of intrinsic heart rate, initiated on a sensed ventricular depolarization; and
delivering a cardioversion or defibrillation pulse to said patient's atrium in response to expiration of said escape interval, in the absence of sensed ventricular depolarizations during said escape interval.

8. A method of atrial cardioversion or defibrillation, comprising: detecting a tachyarrhythmia in a patient's atrium;
sensing depolarizations of said patient's ventricle;
measuring intervals between sensed ventricular depolarizations to derive an interval indicative of intrinsic heart rate;
deriving an escape interval less than said interval indicative of intrinsic heart rate, initiated on a sensed ventricular depolarization; and
delivering a cardioversion or defibrillation pulse to said patient's atrium in response to expiration of said escape interval, in the absence of sensed ventricular depolarizations during said escape interval.

9. A method according to claim 3 or claim 8, wherein said delivering step comprises delivering said cardioversion or defibrillation pulse on expiration of said escape interval, in the absence of sensed ventricular depolarizations during said escape interval.

10. A method of atrial cardioversion or defibrillation, comprising:
detecting a tachyarrhythmia in a patient's atrium;
sensing depolarizations of said patient's ventricle;
measuring intervals between sensed ventricular depolarizations;
deriving an escape interval initiated on a sensed ventricular depolarization, based upon measured intervals between sensed ventricular depolarizations; and
delivering a cardioversion or defibrillation pulse to said patient's atrium in response to expiration of said escape interval, in the absence of sensed ventricular depolarizations during said escape interval; and
delivering a pacing pulse to said patient's ventricle on expiration of said escape interval, in the absence of sensed ventricular depolarizations during said escape interval, and wherein said step of delivering said cardioversion or defibrillation pulse comprises delivering said cardioversion or defibrillation pulse on expiration of a delay interval following expiration of said escape interval.

11. A method according to claim 10, further comprising the step of determining whether said delivered pacing pulse caused a depolarization of said patient's ventricle and the step of preventing delivery of said cardioversion or defibrillation pulse if said pacing pulse does not cause a ventricular depolarization.

12. A method of atrial cardioversion or defibrillation, comprising:
detecting a tachyarrhythmia in a patient's atrium;
sensing depolarizations of said patient's ventricle;
measuring intervals between sensed ventricular depolarizations;
deriving an escape interval initiated on a sensed ventricular depolarization, based upon measured intervals between sensed ventricular depolarizations; and
delivering a cardioversion or defibrillation pulse to said patient's atrium in response to expiration of said escape interval, in the absence of sensed ventricular depolarizations during said escape interval; and
wherein said deriving step comprises determining whether said derived escape interval is less than a minimum interval, and further comprising the step of preventing delivery of said cardioversion or defibrillation pulse if said derived interval is less than said minimum interval.

* * * * *